United States Patent
Lee et al.

(10) Patent No.: US 9,580,677 B2
(45) Date of Patent: Feb. 28, 2017

(54) APPARATUS FOR FILTERING FLUID AND METHODS OF ISOLATING PARTICLE USING THE SAME

(71) Applicant: Samsung Electronics Co., Ltd., Suwon-si, Gyeonggi-do (KR)

(72) Inventors: Hun-joo Lee, Hwaseong-si (KR); Jong-myeon Park, Incheon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 282 days.

(21) Appl. No.: 14/172,576

(22) Filed: Feb. 4, 2014

(65) Prior Publication Data
US 2015/0037831 A1 Feb. 5, 2015

(30) Foreign Application Priority Data
Jul. 30, 2013 (KR) ........................ 10-2013-0090434

(51) Int. Cl.
| | | |
|---|---|---|
| C12N 5/071 | (2010.01) |
| C12M 1/00 | (2006.01) |
| B01D 29/90 | (2006.01) |
| G01N 1/40 | (2006.01) |

(52) U.S. Cl.
CPC ........... *C12M 47/02* (2013.01); *B01D 29/904* (2013.01); *C12N 5/0602* (2013.01); *G01N 1/4077* (2013.01)

(58) Field of Classification Search
CPC ... G01N 1/4077; C12N 5/0602; C12M 47/02; B01L 2300/0867; B01F 2005/0034; B01F 3/0873; B01D 29/904
See application file for complete search history.

(56) References Cited

U.S. PATENT DOCUMENTS

| | | | |
|---|---|---|---|
| 4,894,149 A * | 1/1990 | Block ................. | B01D 24/004 210/101 |
| 6,454,945 B1 | 9/2002 | Weigl et al. | |
| 7,472,794 B2 | 1/2009 | Oakey et al. | |
| 2004/0256318 A1 | 12/2004 | Iida et al. | |
| 2006/0060531 A1* | 3/2006 | Coville ................. | B01D 61/147 210/650 |
| 2006/0068491 A1* | 3/2006 | Makino ............ | B01L 3/502753 435/287.2 |
| 2008/0003689 A1* | 1/2008 | Lee .................... | G01N 30/0005 436/174 |
| 2008/0031832 A1* | 2/2008 | Wakefield ............... | C01G 9/00 424/59 |
| 2008/0201779 A1 | 8/2008 | Tahan et al. | |
| 2010/0323388 A1 | 12/2010 | Chiu et al. | |
| 2011/0097793 A1* | 4/2011 | Suzuki .................. | C12M 47/02 435/325 |
| 2012/0228238 A1 | 9/2012 | Van Rijn et al. | |

(Continued)

FOREIGN PATENT DOCUMENTS

| | | | |
|---|---|---|---|
| JP | 2007/515936 A | 6/2007 |
| JP | 2012/239991 A2 | 12/2012 |

*Primary Examiner* — Christopher A Hixson
(74) *Attorney, Agent, or Firm* — Leydig, Voit & Mayer, Ltd.

(57) ABSTRACT

Provided are an apparatus for filtering a fluid, the apparatus including a first flow channel and a second flow channel which are connected to each other in a fluid communicable manner via a filtration medium, and a method of isolating particles using the apparatus.

12 Claims, 4 Drawing Sheets

(56) References Cited

U.S. PATENT DOCUMENTS

2012/0258529 A1* 10/2012 Lim .................. B01L 3/502746
                                                        435/325
2013/0059288 A1*  3/2013 Dankbar .............. C12Q 1/6806
                                                        435/2

* cited by examiner

APPARATUS FOR FILTERING FLUID AND METHODS OF ISOLATING PARTICLE USING THE SAME

CROSS-REFERENCE TO RELATED APPLICATIONS

This application claims the benefit of Korean Patent Application No. 10-2013-0090434, filed on Jul. 30, 2013, in the Korean Intellectual Property Office, the disclosure of which is incorporated herein in its entirety by reference.

BACKGROUND

1. Field

The present disclosure relates to apparatus for filtering a fluid and methods of isolating a particle by using the same.

2. Description of the Related Art

Fluid isolation methods by filtering a fluid including particles using a filtration medium having a plurality of apertures have been well known in the art. In some cases, however, a layer is formed over time on a surface of a filtration medium by materials accumulated thereon, and thus, the flow of the materials through the apertures may become obstructed. Furthermore, air bubbles may be formed in the apertures, thereby further negatively affecting the flow of materials through the apertures.

Thus, there is a need to develop a method of preventing or removing clogging caused by air bubbles or other materials formed in the apertures of a filtration medium during isolation thereof.

SUMMARY

Provided are apparatuses for filtering a fluid, and methods of efficiently isolating a particle from a sample.

Additional aspects will be set forth in part in the description which follows and, in part, will be apparent from the description, or may be learned by practice of the presented embodiments.

According to an aspect of the present disclosure, an apparatus for filtering a fluid includes: a first flow channel defined by a first inlet disposed at a first end, a second inlet disposed at the opposite side of the first end, and a wall on which a filtration medium is disposed; and a second flow channel connected to the filtration medium in a fluid communicable manner and defined by a first outlet disposed at an opposite side of the filtration medium and walls.

According to another aspect of the present disclosure, there is provided a method of isolating a particle from a sample by using an apparatus for filtering a fluid, the apparatus including: a first flow channel defined by a first inlet disposed at a first end, a second inlet disposed at the opposite side of the first end, and a wall on which a filtration medium is disposed; and a second flow channel connected to the filtration medium in a fluid communicable manner and defined by a first outlet disposed at an opposite side of the filtration medium and walls. The method includes: sequentially flowing the sample including the particle through the first inlet, the first channel, the second channel, and the first outlet of the second channel of the apparatus for filtering a fluid; and sequentially flowing a liquid medium through the second inlet of the first channel, the first channel, the second channel, and the first outlet of the second channel.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
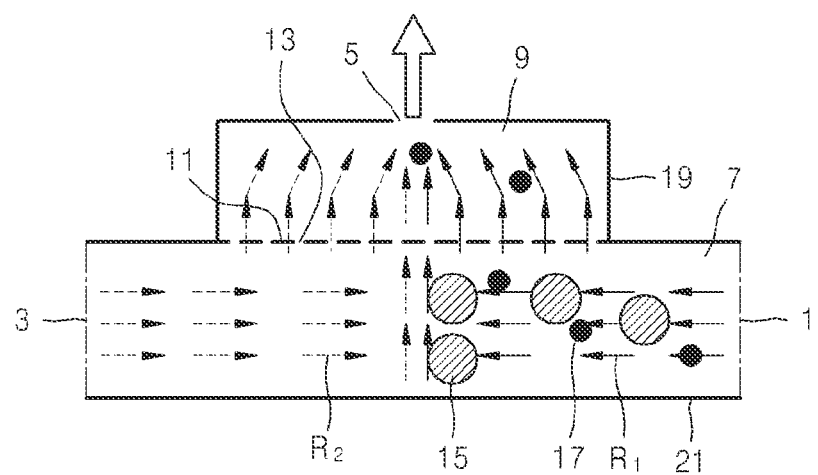
FIG. 1 illustrates an apparatus for filtering a fluid according to an embodiment of the present disclosure.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

According to an embodiment of the present disclosure, there is provided an apparatus for filtering a fluid. The apparatus includes: a first flow channel defined by a first inlet disposed at a first end, a second inlet disposed at a second end opposite the first end, and a wall on which a filtration medium is disposed; and a second flow channel connected to the filtration medium in a fluid communicable manner and defined by walls and a first outlet disposed at a side opposite to the filtration medium.

The apparatus includes the first flow channel defined by a first inlet disposed at a first end, a second inlet disposed at the opposite side of the first end, and a wall on which a filtration medium is disposed. The first flow channel may be a microchannel or nanochannel. For example, at least one portion of a height or width of the first flow channel may have a size of about 1 µm to about 1000 mm, about 1 µm to about 100 mm, about 1 µm to about 10 mm, about 1 µm to about 1 mm, about 1 µm to about 100 µm, about 1 µm to about 10 µm, about 10 µm to about 1000 mm, about 10 µm to about 100 mm, about 10 µm to about 10 mm, about 10 µm to about 1 mm, about 10 µm to about 100 µm, or about 10 µm to about 50 µm. The first flow channel may have a circular or polygonal cross-section.

The filtration medium may have a plurality of apertures. The apertures allow the fluid to flow in a direction from the inside of the first flow channel toward the inside of the second channel or in the opposite direction. An average width or diameter of the apertures may vary according to sizes of particles to be filtered. For example, the average width or diameter may be in the range of about 1 µm to about 100 µm, about 1 µm to about 50 µm, about 1 µm to about 40 µm, about 1 µm to about 30 µm, about 1 µm to about 20 µm, about 1 µm to about 10 µm, about 1 µm to about 5 µm, about 5 µm to about 50 µm, about 10 µm to about 50 µm, about 5 µm to about 40 µm, about 10 µm to about 40 µm, or about 5 µm to about 30 µm. The filtration medium may have more than one aperture, e.g., at least 2, 10, 50, 100, 500, 1000, 5000, 10,000, 50,000, or 100,000 or more apertures.

A flow controller may be connected to at least one of the first and second inlets of the first flow channel. The flow controller may be a valve or a pump. One of the first and second inlets of the first flow channel may be connected to a storage unit storing a liquid medium, e.g., a liquid medium not containing a particle greater than an average width of the apertures of the filtration medium, in a fluid communicable manner. The liquid medium may be water, a buffer solution, an aqueous solution, or any combination thereof. The liquid medium may be used to clean a surface of the filtration medium. For example, the liquid medium may be used to clean or remove a material layer formed on the surface of the filtration medium and having a greater particle size than the average width of the apertures.

In addition, the other of the first and second inlets of the first flow channel may be connected to a sample storage unit including particles. The particles may have a size, e.g., a width or diameter greater than the average width or diameter of the apertures of the filtration medium. The particles may be cells, for example, animal cells. The animal cell may be a cancer cell, for example, a circulating tumor cell (CTC).

At least one portion of the first flow channel may be optically clear. For example, the first flow channel may have an optically clear region through which the filtration medium is observed. The optically clear region may be a thickness direction region of the first flow channel corresponding to a lengthwise direction of the first flow channel occupied by the filtration medium. For example, the optically clear region of the first flow channel may be disposed at an opposite side of the filtration medium. A material of the optically clear region may be glass.

The apparatus may be designed to optically observe the flow of the fluid, which flows through the filtration medium, via the optically clear region. For example, an optical detection device may be disposed in at least one portion of the optically clear region of the first flow channel to correspond to the filtration medium. The optical detection device may be an optical microscope, CCD camera, or a combination thereof.

The apparatus includes the second flow channel connected to the filtration medium in a fluid communicable manner, including the first outlet disposed at the opposite side of the filtration medium, and surrounded by walls. The second flow channel may be a microchannel or nanochannel. For example, at least one portion of a height or width of the second flow channel may have a size of about 1 µm to about 1000 mm, about 1 µm to about 100 mm, about 1 µm to about 10 mm, about 1 µm to about 1 mm, about 1 µm to about 100 µm, about 1 µm to about 10 µm, about 10 µm to about 1000 mm, about 10 µm to about 100 mm, about 10 µm to about 10 mm, about 10 µm to about 1 mm, about 10 µm to about 100 µm, or about 10 µm to about 50 µm. The second flow channel may have a circular or polygonal cross-section.

The first outlet of the second flow channel may be connected to a flow controller. The flow controller may be a valve or a pump.

The apparatus may further include a flow controller connected to at least one of the first and second inlets of the first flow channel and a flow controller connected to the first outlet of the second flow channel. The flow controller may be a valve or a pump.

In the apparatus, the first channel and the second channel may be connected to each other via the filtration medium in a flow communicable manner.

According to another embodiment of the present disclosure, there is provided a method of isolating particles from a sample by using an apparatus for filtering a fluid, the apparatus including: a first flow channel defined by a first inlet disposed at a first end, a second inlet disposed at a second end opposite the first end, and a wall on which a filtration medium is disposed; and a second flow channel connected to the filtration medium in a fluid communicable manner and defined by walls and a first outlet disposed at a side opposite the filtration medium. The method includes: sequentially flowing the sample including the particles through the first inlet, the first channel, the second channel, and the first outlet of the second channel of the apparatus; and sequentially flowing a liquid medium through the second inlet of the first channel, the first channel, the second channel, and the first outlet of the second channel.

The method includes sequentially flowing the sample including the particles through the first inlet of the first channel, the first channel, the second channel, and the first outlet of the second channel of the apparatus for filtering a fluid which includes: a first flow channel defined by a first inlet disposed at a first end, a second inlet disposed at a second end opposite the first end, and a wall on which a filtration medium is disposed; and a second flow channel connected to the filtration medium in a fluid communicable manner and defined by walls and a first outlet disposed at a side opposite the filtration medium. The apparatus for filtering a fluid has been described above.

The flowing of the sample may be performed by applying a negative pressure to the first outlet of the second channel, by applying a positive pressure to the first inlet of the first channel, or both. The pressure may be applied using a pump. The sample may include target particles having a size greater than the average width of the apertures of the filtration medium. Accordingly, the target particles remain in the first flow channel due to their size, and the fluid flows into the second flow channel, thereby isolating the target particles. In this case, the target particles may be collected through the first inlet or the second inlet of the first channel. The target particles may be cells, for example, animal cells. The animal cell may be a cancer cell, for example, a circulating tumor cell (CTC). The sample may be a substance derived from a living organism. The sample may be a substance derived from a living organism including blood, saliva, tissues, or cells. The sample may include target particles having a size smaller than the average width of the apertures. Accordingly, the target particles flow into the second flow channel due to selective permeability through the apertures of the filtration medium, and other particles having a size greater than the average width of the apertures remain in the first flow channel. As a result, the target particles may be isolated. In this case, the target particles may be collected through the first outlet of the second channel.

The method includes sequentially flowing a liquid medium through the second inlet of the first channel, the first channel, the second channel, and the first outlet of the second channel. The flowing of the liquid medium may be performed by applying a negative pressure to the first outlet of the second channel, by applying a positive pressure to the second inlet of the first channel, or both. The pressure may be applied using a pump.

The liquid medium may be water, a buffer solution, an aqueous solution, or any combination thereof. The liquid medium may be used to clean a surface of the filtration medium. For example, the liquid medium may be used to clean or remove a material layer formed on the surface of the filtration medium and having a greater particle size than the average width of the apertures.

The method may further include inducing agitation of a material at the surface of the filtration medium by moving a boundary between a flow of the sample and a flow of the liquid medium with respect to the filtration medium by controlling a flow rate of the sample and a flow rate of the liquid medium. The material layer formed on the surface of the filtration medium may be removed by the agitation. The material layer may include a material having a size greater than the average width of the apertures of the filtration medium, for example, cells or air bubbles. Thus, clogging or air bubbles may be prevented or removed from the apertures of the filtration medium.

The moving of the boundary may be a combination of moving the boundary toward the first inlet and moving the boundary toward the second inlet with respect to the surface of the filtration medium. The moving of the boundary toward the first inlet may be performed by increasing the flow rate of the liquid medium relative to the flow rate of the sample. The moving of the boundary toward the second inlet may be performed by decreasing the flow rate of the liquid medium relative to the flow rate of the sample.

In this method, at least one portion of the first flow channel corresponding to the filtration medium is formed of an optically clear material, and an optical detection device is disposed in the at least one portion of the first flow channel corresponding to the filtration medium and formed of the optically clear material. The method may further include observing the flows of the sample and the liquid medium through the filtration medium using the optical detection device. The method may further include moving the boundary between the flow of the sample and the flow of the liquid medium based on the result of the observation.

The method may further include: stopping the flowing of the sample and the flowing of the liquid medium, after the flowing of the sample including the particles sequentially through the first inlet, the first channel, the second channel, and the first outlet of the second channel of the apparatus and the flowing of the liquid medium sequentially through the second inlet of the first channel, the first channel, the second channel, and the first outlet of the second channel; and isolating target particles, which have not passed through the filtration membrane due to size exclusion, through the second inlet or the first inlet by sequentially flowing the liquid medium through the first inlet, the first channel, and the second inlet of the apparatus or by sequentially flowing the liquid medium through the second inlet, the first channel, and the first inlet of the apparatus.

FIG. 1 illustrates an apparatus for filtering a fluid according to an embodiment of the present disclosure. As illustrated in FIG. 1, the apparatus includes: a first flow channel 7 defined by a first inlet 1 disposed at a first end, a second inlet 3 disposed at a second end opposite the first end, and a wall on which a filtration medium 11 is disposed; and a second flow channel 9 connected to the filtration medium 11 in a fluid communicable manner and defined by walls 19 and a first outlet 5 disposed at a side opposite the filtration medium 11. The filtration medium 11 may have a plurality of apertures 13. The first flow channel 7 and the second flow channel 9 are surrounded by walls 21 and 19, respectively. The apertures 13 of the filtration medium 11 may have an average width that is smaller than a size of the target particles 15 and greater than a size of other particles 17. Accordingly, the target particles 15 are distributed in the first flow channel 7 due to size exclusion by the filtration medium 11, and the fluid is distributed in the second flow channel 9.

The apparatus may further include a flow controller connected to at least one of the first inlet 1 and second inlet 3 of the first flow channel 7 and a flow controller connected to the first outlet 5 of the second flow channel 9. By using the flow controllers, a flow of the sample R1 through the first inlet 1, the first flow channel 7, the filtration medium 11, the second flow channel 9, and the outlet 5 of the second flow channel 9 may be induced, or a flow rate of the sample R1 may be controlled. For example, the flow of the sample R1 may be induced or controlled by applying a negative pressure to the second flow channel 9 using the flow controller, for example, a pump connected to the first outlet 5 of the second flow channel 9, by applying a positive pressure to the first flow channel 7 using the flow controller connected to the first inlet 1 of the first flow channel 7, or both.

In addition, by using the flow controller, a flow of the liquid medium R2 through the first inlet 1, the first flow channel 7, the filtration medium 11, the second flow channel 9, and the outlet 5 of the second flow channel 9 may be induced, or a flow rate of the liquid medium may be controlled. The liquid medium may be a liquid that does not include a target particle, for example, water or a buffer solution. For example, the flow of the liquid medium R2 may be induced or controlled by applying a negative pressure to the second flow channel 9 using the flow controller, for example, a pump connected to the first outlet 5 of the second flow channel 9, by applying a positive pressure to the first flow channel 7 using the flow controller connected to the second inlet 3 of the first flow channel 7, or both. The flow of the sample R1 and the flow of the liquid medium R2 may form a boundary with respect to the surface of the filtration medium 11. The boundary may be moved by controlling the flow rate of the sample R1 and the flow rate of the liquid medium R2. The material disposed or formed on the surface of the filtration medium 11 may be removed by the movement of the boundary. Accordingly, clogging or air bubbles may be removed or prevented on the surface of the filtration medium 11.

Figure 2:
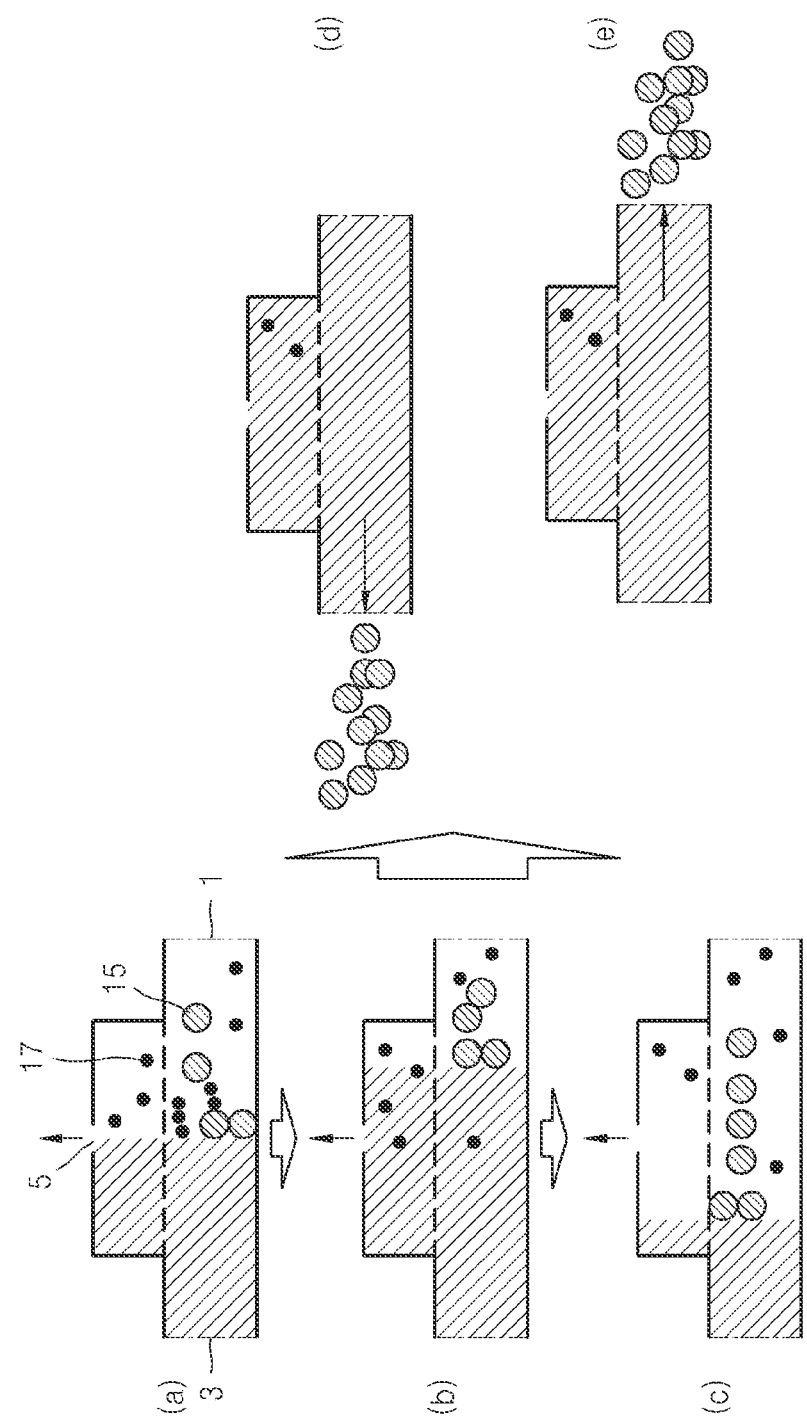
FIGS. 2A to 2E illustrate a method of isolating a target particle by using an apparatus for filtering a fluid according to an embodiment of the present disclosure.

FIGS. 2A to 2E illustrate a method of isolating target particles using an apparatus for filtering a fluid according to an embodiment of the present disclosure. FIG. 2A illustrates that a boundary is formed by a flow of the sample R1 and a flow of the liquid medium R2. In this case, the target particles 15 remain in the first flow channel 7, and particles 17 with a smaller size than the widths of the apertures of the filtration medium pass through the filtration medium and flow into the second flow channel 9. FIG. 2B illustrates a result of increasing the flow rate of the liquid medium R2 or decreasing the flow rate of the sample R1 of FIG. 2A. As a result, the boundary moves toward the first inlet 1 from the surface of the filtration medium. FIG. 2C illustrates a result of increasing the flow rate of the sample R1 or decreasing the flow rate of the liquid medium R12 of FIG. 2A. As a result, the boundary moves toward the second inlet 3 from the surface of the filtration medium. The processes illustrated in FIGS. 2B and 2C may be repeatedly performed. Accordingly, the material layer formed on the surface of the filtration medium may be removed. Accordingly, clogging and air bubbles may be prevented or removed from the apertures of the filtration medium. FIG. 2D illustrates a result of stopping the flowing of the sample R1 and the flowing of the liquid medium R2, and then sequentially flowing the liquid medium through the first inlet 1, the first channel 7, and the second inlet 3 of the apparatus. As a result, the target particles 15 may be collected through the second inlet 3. The flowing of the liquid medium R2 through the first inlet 1, the first channel, and the second inlet 3 may be performed by applying a positive pressure to the first flow channel 7 using the flow controller, for example, a pump connected to the first inlet 1, by applying a negative pressure to the first flow channel 7 using the flow controller, for example, a pump connected to the second inlet 3, or both.

FIG. 2E illustrates a result of stopping the flowing of the sample R1 and the flowing of the liquid medium R2, and then sequentially flowing the liquid medium R2 through the second inlet 3, the first channel 7, and the first inlet 1 of the apparatus. As a result, the target particles 15 may be collected through the first inlet 1. The flowing of the liquid medium R2 through the second inlet 3, the first channel 7, and the first inlet 1 may be performed by applying a positive pressure to the first flow channel 7 using the flow controller, for example, a pump connected to the second inlet 3, by applying a negative pressure to the first flow channel 7 using the flow controller, for example, a pump, connected to the first inlet 1, or both.

Embodiments of the present disclosure will be described in further detail with reference to the following examples. These examples are for illustrative purposes only and are not intended to limit the scope of the invention.

EXAMPLE 1

Isolation of Material by Using Apparatus for Filtering Fluid

An apparatus for filtering a fluid including a first flow channel and a second flow channel, which are connected to each other in a flow communicable manner, was fabricated, and target particles were isolated using the apparatus.

(1) Fabrication of Apparatus for Filtering Fluid

The apparatus for filtering a fluid was fabricated by preparing a filtration membrane that is a filtration medium having a plurality of apertures, interposing the filtration membrane between an upper plate and a lower plate on which at least one portion of each of the first flow channel and the second flow channel is respectively formed, and assembling the structure.

The filtration membrane was prepared using silicon-on-insulator (SOI) techniques. The filtration membrane included circular pores with a uniform pore size of about 8 μm and uniformly spaced apart from each other by about 5 μm. An SOI wafer with a total thickness of about 600 μm included an upper silicon layer with a thickness of about 50 μm and a buried $SiO_2$ layer with a thickness of about 10 μm.

A layer of photoresist AZ 4330 (Clariant Corp., Muttenz, Switzerland) was applied to the SOI wafer, patterned, and etched using deep reactive ion etching (DRIE) for 15 minutes. The opposite Si layer was coated with Photoresist AZ 4330 (Clariant Corp., Muttenz, Switzerland), patterned, and etched using an 8% tetramethyl ammonium hydroxide (TMAH) solution. Then, the buried $SiO_2$ layer was etched using a 10% hydrofluoric acid solution. Finally, the photoresist was peeled off, and the wafer was cut in 10 mm by 10 mm squares. Pores were respectively formed within 5 mm by 5 mm squares in 10 mm by 10 mm squares.

Figure 3:
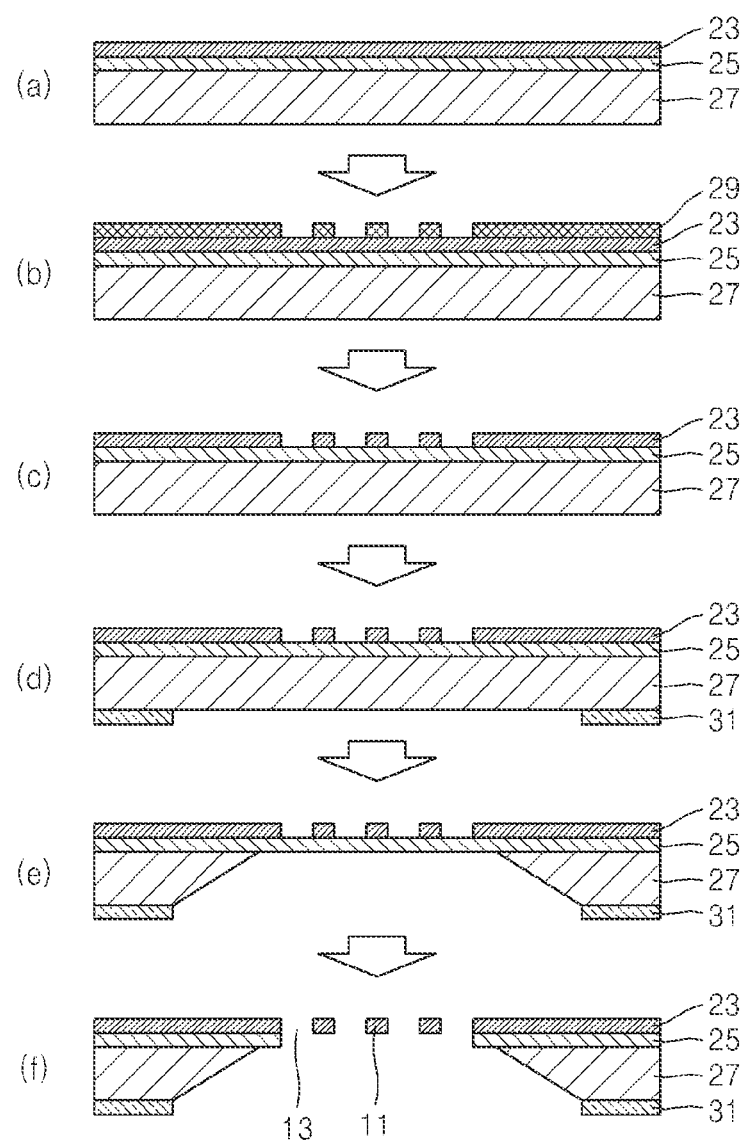
FIG. 3A to 3F illustrate a process of preparing a filtration membrane by using a silicon-on-insulator (SOI) technique according to an embodiment of the present disclosure.

FIGS. 3A through 3F illustrate a process of preparing a filtration membrane by using a silicon-on-insulator (SOI) technique according to an embodiment of the present disclosure. Referring to FIGS. 3A, 3B, 3C, 3D, 3E, and 3F respectively illustrate an SOI wafer and photoresist coating, patterning of a photoresist 29, RIE etching, patterning of a photoresist 31, backside etching, and $SiO_2$ etching. Referring to FIG. 3A, the SOI wafer has a stack structure in which a silicon layer 23, a $SiO_2$ layer 25, and a silicon layer 27 are laminated. As a result, a filtration membrane 11 having pores 13 is formed. The filtration membrane may be fabricated by the following procedures: (a) making SOI wafer: the SOI wafer was fabricated by silicon-on-insulator (SOI) technology and specifically designed in-house to maximize the number of uniform-sized (pore diameter: about 8 μm), evenly spaced (distance between pores: about 5 μm) circular pores. The SOI wafer with about 600 μm total thickness consists of 50 μm top silicon layer 23, and 10 μm buried SiO2 layer 25, and 50 μm bottom silicon layer 27. (b) photoresist patterning: photoresist AZ 4330 (Clariant Corp., Muttenz, Switzerland) was coated on the top silicon layer 23 with a spin coating method, and patterned by photolithography to selectively remove portions of the photoresist, and the photoresist was removed. (c) top silicon layer etching: deep reactive-ion etching (DRIE) was performed to the top silicon layer 23 for 15 min to selectively etch the top silicon layer 23 and remove the photoresist. (d) backside photoresist patterning: The bottom silicon layer 27 was coated with a photoresist AZ 4330 (Clariant Corp., Muttenz, Switzerland) 31 with spin coating and patterned by photolithogy. (e) bottom silicon layer 27 wet etching: the bottom silicon layer 27 wet etched with 8% tetramethylammonium hydroxide (TMAH), and (f) SiO2 layer 25 etching: the buried SiO2 layer 25 was etched with 10% solution of hydrofluoric acid. Finally, the photoresist 31 was stripped off and the wafer was cut to a square of 10 mm×10 mm.

Figure 4:
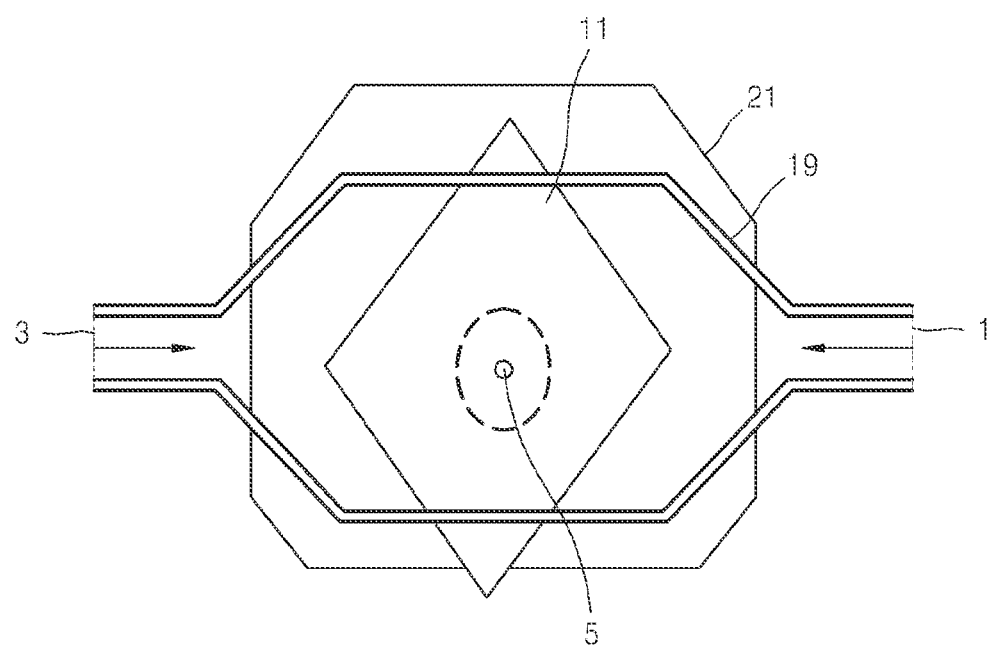
FIG. 4 illustrates an apparatus for filtering a fluid according to an embodiment of the present disclosure.

FIG. 4 illustrates a prepared apparatus for filtering a fluid. The prepared filtration membrane 11 is disposed between a lower plate 21 on which the first flow channel 7 is formed and an upper plate 19 on which the second flow channel 9 having the second outlet 5 is formed, and the structure is assembled to fabricate the apparatus for filtering a fluid. The first flow channel 7 has a height of about 200 μm and a length of about 5 mm, and the second flow channel 9 has a length of about 2.5 mm and a height of about 1 mm.

(2) Isolation of Material by Using the Apparatus for Filtering Fluid

Target particles were isolated using the apparatus for filtering a fluid fabricated according to Operation (1) above. Melamine resin-based FITC-labeled particles with a particle size of 3 μm (Fluka 72439) were used as the target particle. 3 mL of a PBS solution including the target particles was used as a sample. The concentration of the target particles was 0.025% (w/v PBS).

The first inlet 1 of the first flow channel 7 was connected to a container including the sample, the second inlet 3 of the first flow channel 7 was connected to a container including the PBS solution, and a syringe pump was connected to the first outlet 5 of the second flow channel 9. Then, a fluid was flowed at a rate of about 500 μL/min through the first outlet 5 of the second flow channel 9 through the syringe pump, and a positive pressure was applied to a syringe pump connected to the second inlet 3 of the first flow channel 7 to flow the PBS solution through the second inlet 3 at a rate of about 50 to about 450 μL/min. The flow rate repeatedly varied from about 50 μL/min to about 450 μL/min, such that the boundary between the sample and the buffer solution moved between both ends of the filtration membrane at a rate of 6 times/min. In total, the reciprocating movements were performed 36 times. Then, the target particles contained in the fluid and collected through the first outlet 5 of the second flow channel 9 were identified by measuring a fluorescence intensity at 525 nm. As a control group, the PBS solution was flowed through the second inlet 3 at a rate of 250 μL/min without moving the boundary by uniformly applying a positive pressure to the syringe pump connected to the second inlet 3 of the first flow channel 7. Pores of the filtration membrane used herein had a diameter of 8 µm.

As a result, while the control group exhibited a fluorescence intensity of 27.60, the experimental group exhibited a fluorescence intensity of 4.32. Thus, by continuously moving the boundary using the liquid medium not including the target particles, for example, a buffer solution, through the second inlet 3, a filtration efficiency was considerably increased. Hence, it is reasonable to infer that this was induced by the flow of the liquid medium that flowed through the second inlet 3 and removed the material layer or air bubbles formed on the surface of the filtration membrane by agitation.

(3) Isolation of Material by Using Apparatus for Filtering Fluid: Isolation Using Size Exclusion Then, isolation of target particles by size exclusion was tested using a sample including target particles having a size greater than a width of the pores of the filtration membrane of the apparatus for filtering the fluid fabricated according to Operation (1) above and other particles having a size smaller than the width of the pores.

2.5 mL of a PBS solution including melamine resin-based FITC-labeled particles with a particle size of 3 µm (Fluka 72439) and melamine resin-based carboxylate-modified rhodamine B-labeled particles with a particle size of 10 µm (Sigma 88893) was used as a sample. The concentration of each of the particles was 0.025% (w/v PBS).

The first inlet 1 of the first flow channel 7 was connected to a container including the sample, the second inlet 3 of the first flow channel 7 was connected to a container including the PBS solution, and a syringe pump was connected to the first outlet 5 of the second flow channel 9. Then, a fluid was flowed through the first outlet 5 of the second flow channel 9 through the syringe pump at a rate of about 500 µL/min, and a positive pressure was applied to a syringe pump connected to the second inlet 3 of the first flow channel 7 to flow the PBS solution at a rate of about 50 to about 450 µL/min through the second inlet 3. The flow rate repeatedly varied from about 50 µL/min to about 450 µL/min, such that the boundary between the flow of the sample and the flow of the buffer moved between both ends of the filtration membranes at a rate of 6 times/min. In total, the reciprocating movements were performed 36 times. Then, the particles with a particle size of 3 µm contained in the fluid and collected through the first outlet 5 of the second flow channel 9 was identified by measuring a fluorescence intensity at an excitation wavelength of 490 nm and an emission wavelength of 525 nm, and the particles with a particle size of 10 µm were identified by measuring a fluorescence intensity at an excitation wavelength of 540 nm and at an emission wavelength of 584 nm. As a control group, the PBS solution was not flowed through the second inlet 3 by stopping application of the positive pressure to the syringe pump connected to the second inlet 3 of the first flow channel 7. Pores of the filtration membrane used herein had a diameter of 8 µm.

The results are shown in Table 1 below.

TABLE 1

| Particle (µm) | Fluorescence intensity (RU) | |
|---|---|---|
| | Experimental group | Control group |
| 3 | 4.30 | 29.61 |
| 10 | 241 | 243 |

As shown in Table 1, the concentration of the 3 µm particles of the control group was considerably greater than that of the experimental group. Thus, it was confirmed that the particles moved from the first flow channel to the second flow channel through the filtration membrane by agitation caused by the boundary movement. On the other hand, since the concentrations of the 10 µm particles of the control group and the experimental group were not significantly different, it was confirmed that the 10 µm particles remained in the first flow channel. As a result, the 3 µm particles smaller than the diameter of the pores may flow into the second flow channel. Thus, the 10 µm as target particles may be isolated from the 3 µm particle.

In addition, the apparatus was operated with respect to the 10 µm particles for 2.5 minutes under the same conditions as in the experimental example, and then 1 mL of the PBS solution was flowed toward the first inlet 1 from the second inlet 3 of the first flow channel at a rate of 20 ml/min to collect non-filtered 10 µm particles. 10 µm particles contained in the collected solution were counted using a microscope with a magnification of 40×. As a result, it was confirmed that 98% of the initial number of 10 µm particles contained in the sample was collected.

As described above, according to the one or more of the above embodiments of the present disclosure, the apparatus for filtering a fluid may be efficiently used to isolate target particles without being affected by clogging and formation of an air bubble layer.

According to the method of isolating particles from a sample according to the one or more of the above embodiments of the present disclosure, target particles may be efficiently isolated from a sample.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of isolating a particle from a sample using an apparatus for filtering a fluid, the apparatus comprising: a first flow channel defined by a first inlet disposed at a first end, a second inlet disposed at a second end opposite the first end, a filtration membrane having a plurality of apertures, and a wall on which the filtration membrane is disposed; and a second flow channel connected to the filtration medium in a fluid communicable manner and defined by walls and a first outlet disposed at a side opposite the filtration membrane, the method comprising:

sequentially flowing a sample comprising the particle through the first inlet, the first channel, the second channel, and the first outlet of the second channel of the apparatus for filtering a fluid; and simultaneously with the sequentially flowing the sample, sequentially flowing a liquid medium through the second inlet of the first channel, the first channel, the second channel, and the first outlet of the second channel.

2. The method of claim 1, wherein the flowing of the sample is performed by one or both of applying a negative pressure to the first outlet of the second channel, and applying a positive pressure to the first inlet of the first channel.

3. The method of claim 1, wherein the flowing of the liquid medium is performed by one or both of applying a negative pressure to the first outlet of the second channel, and applying a positive pressure to the second inlet of the first channel.

4. The method of claim 2, wherein the pressure is applied by a pump.

5. A method of isolating a particle from a sample using an apparatus for filtering a fluid, the apparatus comprising: a first flow channel defined by a first inlet disposed at a first end, a second inlet disposed at a second end opposite the first end, and a wall on which a filtration medium is disposed; and a second flow channel connected to the filtration medium in a fluid communicable manner and defined by walls and a first outlet disposed at a side opposite the filtration medium, the method comprising:
  sequentially flowing a sample comprising the particle through the first inlet, the first channel, the second channel, and the first outlet of the second channel of the apparatus for filtering a fluid;
  sequentially flowing a liquid medium through the second inlet of the first channel, the first channel, the second channel, and the first outlet of the second channel; and
  inducing agitation of a material at the surface of the filtration medium by moving a boundary between a flow of the sample and a flow of the liquid medium with respect to the filtration medium by controlling a flow rate of the sample and a flow rate of the liquid medium.

6. The method of claim 5, wherein a material layer formed on the surface of the filtration medium is removed by the agitation.

7. The method of claim 5, wherein the moving of the boundary comprises a combination of moving the boundary toward the first inlet and moving the boundary toward the second inlet with respect to the surface of the filtration medium.

8. The method of claim 1, wherein a size of the particle is greater than a diameter of each aperture.

9. The method of claim 1, further comprising observing the flows of the sample and the liquid medium through the filtration membrane using an optical detection device,
  wherein at least one portion of the first flow channel corresponding to the filtration membrane is formed of an optically clear material, and the optical detection device is disposed in the at least one portion of the first flow channel corresponding to the filtration membrane and formed of the optically clear material.

10. The method of claim 5, further comprising observing a boundary between the flow of the sample and the flow of the liquid medium through the filtration medium by using an optical detection device,
  wherein at least one portion of the first flow channel corresponding to the filtration medium is formed of an optically clear material, and the optical detection device is disposed in the at least one portion of the first flow channel corresponding to the filtration medium and formed of the optically clear material.

11. The method of claim 10, further comprising moving the boundary between the flow of the sample and the flow of the liquid medium based on an observation result.

12. The method of claim 3, wherein the pressure is applied by a pump.

* * * * *